United States Patent
Inoue et al.

(10) Patent No.: US 6,224,684 B1
(45) Date of Patent: May 1, 2001

(54) METHOD FOR PREPARING RAFFINOSE CRYSTALS AND EQUIPMENT FOR THE SAME

(75) Inventors: Hiroshi Inoue, Kanagawa-ken; Yoshihiro Semba, Yamaguchi-ken; Osamu Suda; Yuichi Ohwada, both of Hokkaido, all of (JP)

(73) Assignee: Nippon Tensaiseito Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/265,546

(22) Filed: Mar. 9, 1999

(51) Int. Cl.$^7$ .................................................. C13F 1/02
(52) U.S. Cl. .................................................. 127/60
(58) Field of Search .................................................. 127/60

(56) References Cited

U.S. PATENT DOCUMENTS

| | | | |
|---|---|---|---|
| 3,506,486 | * | 4/1970 | Ganiaris ................................. 127/58 |
| 4,145,230 | * | 3/1979 | Madsen et al. ........................ 127/60 |
| 4,666,527 | * | 5/1987 | Ito et al. ................................ 127/60 |

FOREIGN PATENT DOCUMENTS

| | | |
|---|---|---|
| 5236793 | 6/1994 | (AU) . |
| 1321771 | 6/1971 | (GB) . |
| 1406170 * | 6/1988 | (SU) ...................................... 127/60 |

OTHER PUBLICATIONS

Vaccari et al., "Cooling Crystallization Applied to the "Extract", Fraction of a Chromatographic Separation Process (SMB) of Molasses", *Proceedings of the Conference on Sugar Processing Research*, pp. 93–108, (1998).
XP–002112995, Derwent Publication Ltd., Feb. 17, 1998.
XP–002112996, Derwent Publication Ltd., Mar. 23, 1999.

* cited by examiner

*Primary Examiner*—David Brunsman
(74) *Attorney, Agent, or Firm*—Browdy and Neimark

(57) ABSTRACT

By a process of crystallizing raffinose under cooling, raffinose is efficiently crystallized, by continuously or intermittently circulating a solution containing raffinose, whereby temperature control can be done rapidly and accurately and laborious works for removing raffinose crystals adhered to the container are never needed because raffinose crystals are not adhered to the crystallization container under cooling, leading to the elevation of the yield, so the invention is excellent as a system for producing raffinose crystals industrially, in particular.

16 Claims, 3 Drawing Sheets the rate of temperature decrease can be effected, and therefore an efficient crystallization of

METHOD FOR PREPARING RAFFINOSE CRYSTALS AND EQUIPMENT FOR THE SAME

DETAILED DESCRIPTION OF THE INVENTION

1. Technical Field to which the Invention Belongs

The present invention relates to the crystallization of raffinose by cooling a raffinose-containing solution; more specifically, the invention relates to a system particularly suitable for industrial and large-scale crystallization of raffinose by cooling a solution containing raffinose at a high concentration, thereby crystallizing raffinose efficiently, with no strong adhesion of raffinose crystals to the wall of a container or the like.

From an industrial standpoint, in particular, the invention is very useful, for example, for separating and concentrating a raffinose-containing fraction from beet molasses and the like and subsequently crystallizing raffinose under cooling.

2. Prior Art

A technique for crystallizing raffinose, comprising subjecting discard molasses to a chromatographic separation process to isolate the raffinose component, has been known in JP-B-56-39640. This comprises subjecting beet molasses to chromatographic separation and concentrating a raffinose fraction (at a sucrose/raffinose ratio equal to or smaller than 2) to rBx 60.8 to 70 to recover a raffinose-concentrated solution, and leaving the solution to stand overnight under gentle agitation to crystallize and separate the crystals. However, the raffinose crystallization method is not suitable for efficiently generating a vast amount of raffinose crystals.

Problems to be solved by the Invention

So as to efficiently generate a vast amount of raffinose crystals industrially, the crystallization ratio should necessarily be elevated. As shown in FIG. 1, pure raffinose is characteristically of a low solubility at low temperatures; and by utilizing the characteristics, raffinose is crystallized at a crystallization process under cooling. More specifically, the solubility of raffinose is significantly reduced when the temperature of a solution containing raffinose is lowered to 50° C. or less, so it can be said that the temperature range is preferably retained so as to elevate the crystallization efficiency. Furthermore, the efficient transmission of the temperature within the range to a solution containing raffinose at a high concentration is a key factor for the elevation of the crystallization efficiency.

Accordingly, an equipment and a crystallization method capable of satisfying the conditions are desired.

MEANS FOR SOLVING THE PROBLEMS

Figure 1:
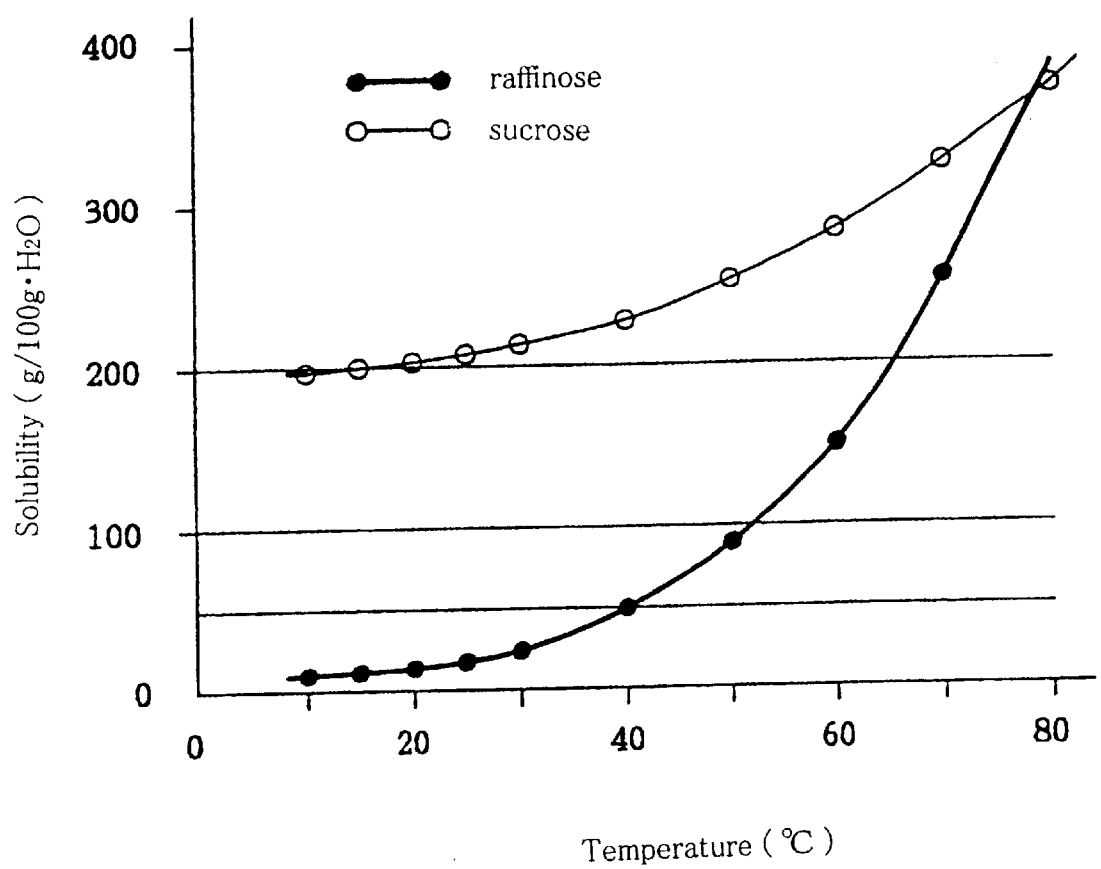
FIG. 1 shows graphs depicting the relation between raffinose solubility and temperature and the relation between sucrose solubility and temperature.

So as to attain the object, the invention has been achieved. In accordance with the invention, a novel equipment for cooling and crystallization of raffinose and a new method for producing raffinose crystals are created for the recovery of the crystals.

The present inventors have drawn their attention to the balance between the rate of temperature decrease and the crystal growth rate when a solution containing raffinose at a high concentration is cooled, while the inventors have also focused their attention to highly efficient transmission of the temperature for cooling to the solution containing raffinose at a high concentration.

When the rate of temperature decrease in a solution containing raffinose at a high concentration is too large, false grains or conglomerates may potentially emerge; when the rate is too small,. the growth of the crystals is slowed down. When a solution containing raffinose at a high concentration is cooled, additionally, the crystals are adhered to the inside of an equipment for cooling and crystallization. Once the crystals are adhered, then, the temperature transmission is blocked; additionally, accurate liquid temperature cannot be caught rapidly and therefore, a far longer time is needed until the designated liquid temperature is reached; or a delicate temperature control cannot be effected.

Furthermore, crystals once adhered can never be removed in a simple manner, and a vast amount of laborious works is required to peel off the crystals from the inside of the equipment for cooling and crystallization; and such crystals work as a serious industrial barrier.

The crystal adhesion cannot be prevented by only agitating a solution containing raffinose, but the crystals are adhered to an agitator too. Thus, the intended purpose cannot be attained.

From a standpoint for the development of a new technique for preventing crystal adhesion for raffinose crystallization under cooling in light of industrial aspects, therefore, the inventors have made attempts to develop a technique for preventing crystal adhesion, the technique being suitable for a process on an industrial large scale. The inventors have intended to establish a method for efficiently producing raffinose crystals.

As the outcome of investigations in various fields, totally unexpectedly, the inventors have found such a useful finding, amazing and new, that raffinose crystals are never adhered to the equipment for cooling and crystallization of raffinose, when a solution containing raffinose is drawn out of a container and is then returned through a circulation pump into the container, thereby circulating the solution containing raffinose.

Consequently, an efficient crystallization process even in a large-volume tank is firstly established by delicately controlling the temperature decrease in a solution containing raffinose, even though the solution contains raffinose at a high concentration, so that the recovery ratio of raffinose from molasses can be elevated prominently on an industrial scale. Thus, the invention has been attained.

In other words, in accordance with the invention, raffinose crystallization is efficiently promoted, by cooling a solution containing raffinose to which raffinose crystal growing seed is added, in a container equipped with a cooling part, under agitation or non-agitation while continuously or intermittently drawing the solution from the container and returning the drawn solution into the container for circulation, while cooling the solution in the container. Another solution containing raffinose prepared similarly to which raffinose crystal growing seed has been added, may be further added (fed) into the container, after the addition of the seed previously-mentioned, apart from or after mixing with the above-mentioned drawn solution, and the resulting solution in the container is circulated similarly as above-mentioned. Thus, the adhesion of raffinose crystals to the equipment can be prevented, and an accurate and rapid control of temperature can be effected, and therefore an efficient crystallization of raffinose can be attained. Said another solution containing raffinose may be identical with, the same as or different from the previously-mentioned seed-added solution containing raffinose to be drawn for the circulation. An example of said another solution is a solution of different container or lot.

Namely, the primary method of the present invention is as follows:

A method for producing raffinose crystal, which comprises (1) feeding a solution containing raffinose into a container equipped with a cooling part;
(2) cooling the solution;
(3) adding raffinose crystal growing seed thereto; and
(4) circulating the seed-added solution continuously or intermittently by drawing from the container, passing through a pipe and returning into the container, while cooling the seed-added solution.

And a method of the present invention dependent on said primary method is the method wherein the above-mentioned another solution is further added in said primary method, as above-explained.

The term "seed" means a liquid in which powdery raffinose is suspended; i.e., raffinose does not dissolve therein (e.g., absolute ethyl alcohol may be used therefor).

The invention will now be described in detail.

Figure 2:
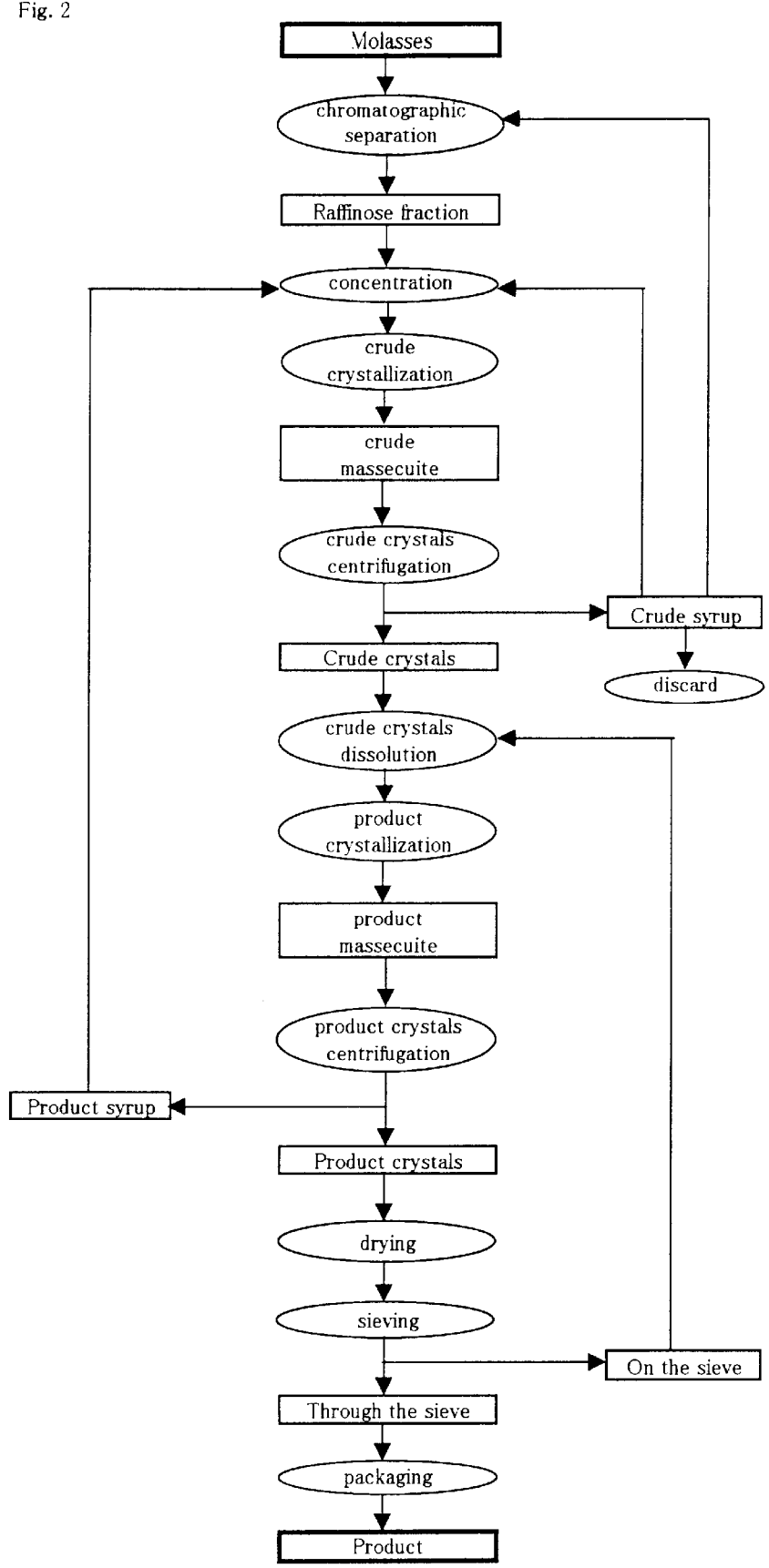
FIG. 2 is a flow chart of the raffinose production process.

Raffinose is contained in beet molasses and the like, and raffinose has been believed as one of impurities during the production of beet sugar. In recent years, however, it has been discovered that raffinose has an action to rhythmically promote or suppress the motion of colon as well as other actions. Accordingly, attention is now focused on the usefulness of raffinose, but not any synthetic method thereof with no problem from the aspect of safety profile has been developed yet; up to now, raffinose has been produced by an extraction method from a raw material beet molasses (FIG. 2); but the molasses contains an extremely low content of raffinose. As has been described above, thus, a method for efficiently crystallizing raffinose has been demanded in the industry.

In accordance with the invention, raffinose crystals can be produced in an efficient manner from a solution containing raffinose; the solution containing raffinose includes any of all solutions containing raffinose; and as one representative example thereof, a solution containing beet molasses-derived raffinose at a high concentration is exemplified so as to describe the invention in detail.

In accordance with the invention, the term molasses means green syrup generated during the separation of sugar massecuite at the production process of beet sugar; and the green syrup includes a first green syrup, a second green syrup, a third green syrup and discard molasses. In order to attain an efficient crystallization of raffinose, a solution containing raffinose at a high concentration in the present invention means a solution containing raffinose at a high concentration of which the supersaturation degree (at 50 to 70° C.) is 0.5 to 1.0, of which the raffinose purity is 60 to 99 SD %, and of which the rBx (at 20° C.) is 60 or less, as explained hereinafter. The term SD % represents percentage by weight of raffinose contained in the dry solid of the solution. The supersaturation degree of a solution containing raffinose at a temperature is obtained by the following formula:

[Supersaturation degree]=A/B

A=[Amount of raffinose in the solution at 20° C. (amount unit: g) ]/[Amount of water in the solution at 20° C. (amount unit: g)

B=[Solubility of raffinose at the temperature (g/100 g $H_2O$)]/100 (g: amount of water)

The solubility of raffinose is shown in FIG. 1. The examples of the solution containing raffinose at a high concentration are (1) a concentrate of one member selected from the group consisting of (a) the raffinose fraction, (b) the crude syrup and (c) the product syrup, (2) a concentrate of a mixture of at least two members selected from said group, (3) a solution prepared by dissolving the crude crystals, and (4) a solution prepared by dissolving the raffinose on the sieve (cf. FIG. 2), etc.

Figure 3:
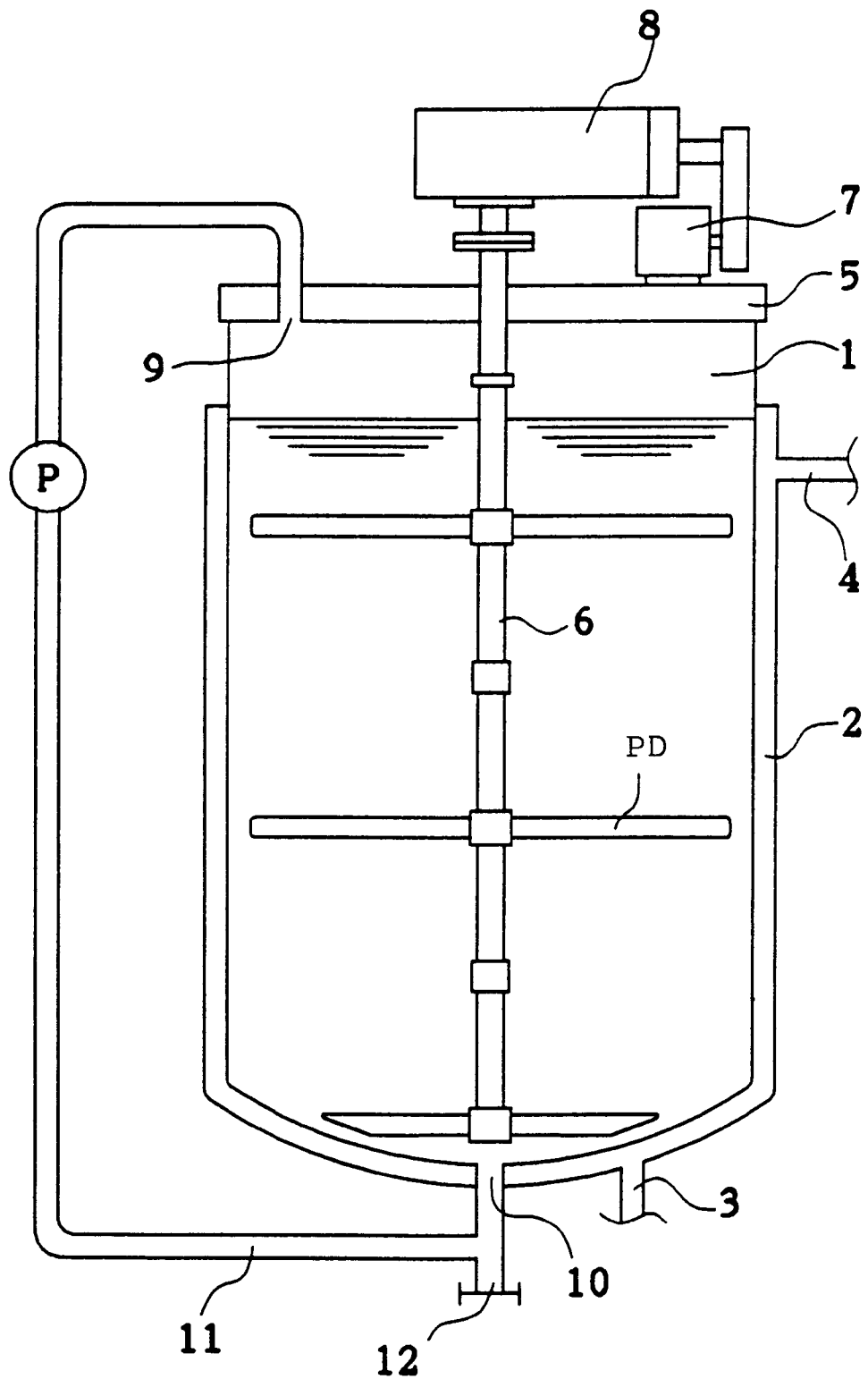
FIG. 3 shows an equipment for cooling and crystallization.

So as to practice the invention, preferably, the solution containing raffinose at a high concentration is treated by using an equipment for crystallizing raffinose under cooling in accordance with the invention; and one example of the equipment for crystallizing raffinose under cooling in accordance with the invention is shown in FIG. 3.

The solution containing raffinose at a high concentration is placed in container 1 equipped with a cooling part. One or more of jacket system, calandria system, coil system and the like may appropriately be used as the cooling equipment of the solution; in the present example, the jacket system is adopted; by arranging jacket 2 on the exterior side of container 1, feeding cooling water, a cooling solvent, cooling air and the like under temperature control from jacket inlet 3 and drawing out them from jacket outlet 4, the solution is cooled to a given temperature.

Lid 5 is arranged on the upper part of container 1. On lid 5 are arranged motor 7 for driving agitator 6 and speed reducer 8. Agitator 6 is equipped with paddle PD. In the figure, three paddles are depicted, but the number, arranging place and shape of the paddles may be arbitrary, satisfactorily. The end of the lower part of each paddle is satisfactorily closer to the inner wall of container 1, but a scraper (not shown in the figure) may satisfactorily be arranged on the end of each paddle PD, so that crystals possibly adhered to the inner wall can be scraped off, if necessary.

On lid 5 may satisfactorily be arranged a manhole (not shown in the figure), so that the solution might be supplied therethrough or an operation personnel might be entered therethrough in or out of the container. 9 is an in-port for feeding the solution drawn out from out-port 10 arranged on the bottom of container 1 into container 1. Out-port 10 and in-port 9 are connected together through circulation pump P with pipe 11.

To the solution containing raffinose at a high concentration under cooling, is added raffinose crystal growing seed, and the seed-added solution is further cooled down to a given temperature by means of the jacket (cooling part). Meanwhile, the solution in the container is drawn from out-port 10, passed through pipe 11 and returned through in-port 9 into container 1, for intermittent or continuous circulation of the solution under cooling and agitating; it is better to drive agitator 6 from the start of the production of raffinose crystals. The solution drawn from the container, is fed into the container for the circulation, while cooling the solution in the container. Another solution containing raffinose at a high concentration prepared similarly to which raffinose crystal growing seed has been added, may be further added (fed) into the container, after the addition of the seed above-mentioned, apart from or after mixing with the above-mentioned solution drawn from the container, and the resulting solution in the container is circulated similarly as above-mentioned. Said another solution containing raffinose at a high concentration may be identical with, the same as or different from the seed-added solution containing raffinose at a high concentration above-mentioned. An example of the said another solution further added is a solution of different container or lot.

By such a circulation process of the solution, the crystal adhesion to the inner wall of the container and the agitator and the like can be prevented; furthermore, the effect on the prevention of the crystal adhesion can further be enhanced by rotating agitator 6. When the agitation is singly done with no circulation of the solution, the crystals are adhered, so that the intended object cannot be attained.

After the termination of the cooling and crystallization process in such a manner, out-port 10 is opened, to discharge a solution containing formed raffinose crystals (i.e., massecuite) from discharge port 12 arranged on pipe 11. In the example, a single port bifunctionally works as out-port 10 and discharge port 12, but the two ports may satisfactorily be arranged separately. Herein, discharge port 12 may satisfactorily be arranged on the lowest bottom of container 1 from the respect of the prevention of scaling and contamination.

In accordance with the invention, the circulation of the massecuite (a solution of the raffinose crystals adhered by cooling the solution containing raffinose at a high concentration as mixed with the mother liquor) is indispensable as described above, because the fluidity of the solution can then be retained by keeping the crystals at such a state of marginally homogeneous dispersion in the solution by means of the circulation pump so as to avoid the adhesion of the crystals in the cooling equipment; and the agitator additionally functions to supplement the circulation.

So as to keep the appropriately dispersed state, suitably, the rotation velocity of the agitator is 5 to 20 rpm and that the flow rate of the circulation pump is 1 to 3 BV/Hr (BV/Hr means a flow rate at which a solution inside is exchanged once per one hour).

The crystallization of raffinose under cooling is effected in a batchwise manner or continuously. Just when the liquid temperature of the solution containing raffinose at a high concentration reaches 35 to 50° C., raffinose crystal growing seed (referred to as seed hereinbelow) is added to the solution, and by subsequently lowering the temperature in approximately inverse proportion to the time over 10 to 50 hours, the temperature is finally adjusted to 18 to 22° C. From the respect of the prevention of scaling on the cooling part, in particular, the aforementioned conditions are appropriate.

The rBx of the solution containing raffinose at a high concentration in the cooling equipment is 60 at maximum, and the supersaturation degree thereof is appropriately 0.5 to 1.0. Above rBx 60, the viscosity thereof in the equipment for cooling and crystallization is increased, leading to significant reduction of the fluidity, so that crystallization topically occurs. Above a supersaturation degree of 1.0, the crystal growing rate is too large to keep a balance with the rate of temperature decrease. In any of the cases, the discharge of the massecuite from the equipment for cooling and crystallization involves much difficulty; and additionally, the supersaturation degree works to cause the increase of scaling in the cooling part.

At a supersaturation degree less than 0.5, crystallization less occurs, with the resultant low crystal yield, leading to the reduction of the processability. Most of the solutions containing raffinose at a high concentration in the present invention have rBx of 30 to 60. Even if rBx of a solution containing raffinose is less than 30, the solution having supersaturation degree of 0.5 to 1.0 and raffinose purity of 60 to 99 SD % is the solution containing raffinose at a high concentration in the present invention.

Mechanically, the discharge port of the massecuite solution should necessarily be arranged on the lowest bottom of the equipment for cooling and crystallization. By the presence of the discharge port at such lowest bottom, the residual solution in the equipment for cooling and crystallization is suppressed at minimum. Therefore, the prevention of scaling and the prevention of contamination can be established at the port.

EXAMPLE

Detailed description will be made in the following example.

A molasses (rBx 80) generated during the production of beet sugar through a demineralizing process was used. The concentration thereof was diluted to rBx60 and was then passed through a simulated moving bed equipment employing a multi-component separation system at a temperature of about 80° C., to separate the multi components (raffinose fraction, sweet oligo fraction, sucrose fraction, betaine fraction, and other fractions) from each other.

The raffinose fraction herein referred to means a raffinose rich fraction of which the solid content is 5 to 8% and of which the raffinose purity is 60 to 70 SD %.

A mixture solution at a mixture ratio (solid ratio) of the raffinose fraction :crude syrup : product syrup being 12:7:1 was prepared, which was then concentrated in a falling film-type concentration can to a final rBx of 58.

Herein, the components of the individual materials are as follows.

Unit: SD %.

|  | rBx | Raffinose | Sucrose |
| --- | --- | --- | --- |
| Discard molasses | 79 | 12 | 57 |
| Raffinose fraction | 6 | 62 | 5 |
| Crude syrup | 44 | 44 | 7 |
| Product syrup | 29 | 93 | 3 |
| Crude massecuite | 58 | 57 | 6 |
| Product massecuite | 58 | 98 | 1 |

As a container for cooling and crystallization, a cylindrical container equipped with a cooling jacket as shown in FIG. 3 was used. The container is of a structure equipped with an agitator with paddles and a circulation pump for circulating a solution from the lowest part of the container to the top of the container. While driving the agitator, the above-mentioned concentrated solution containing raffinose (rBx: 58, raffinose purity: 57 SD % and super-saturation degree: 0.9 at 50° C. ) was fed at a feed rate of 250 L/H, in the container of an inner volume of 6.5 m$^3$, to a level of about 80% of the volume. After feeding the solution, raffinose crystal growing seed (seed 2 L/5.0 m$^3$ of the solution) was added to the solution just when the solution temperature reached 37° C. The term seed herein means seed produced by dispersing one kg of raffinose crystals pulverized with a ball mill for 3 hours in 2 liters of 99% ethyl alcohol.

Then, the solution temperature was decreased in approximately inverse proportion to the time course over 40 hours to a final temperature of 20° C. At the agitation velocity of the agitator at 10 rpm and the circulation rate by means of the circulation pump at 2 BV/hr, the state of the raffinose crystal solid in dispersion in the mother liquor was consistently kept.

By subsequently separating the crude massecuite (at a raffinose purity of 57 SD %) into the crystals and syrup by means of a separator, crude raffinose crystals (at a raffinose purity of 98 SD %) were recovered.

The crystallization ratio of crude crystals was calculated under the conditions. As a result, the ratio was 41%.

The crude crystals were again dissolved in warm water, followed by recrystallization under cooling, to recover a product massecuite (at rBx 58 and a raffinose purity of 98 SD %). Through subsequent separation with a centrifugal separator, product crystals (at a raffinose purity of 99.5 SD %) and a product syrup (at a raffinose purity of 93 SD %) were recovered. The crystallization ratio of product crystals was calculated as 78%.

The crystallization ratio was calculated by the following formula.

Ratio of raffinose crystallization=[crystal purity×{(purity of massecuite)−(purity of syrup)}]×100/[purity of massecuite×{(crystal purity)−(purity of syrup)}]

Advantages of the Invention

Crystallization processes under cooling have conventionally been employed for raffinose crystallization, but no detailed description of the crystallization processes has been published yet; and such processes have been applied to the production of raffinose on a small scale. The invention relates to a method for recovering raffinose crystals on an industrially large scale, and an equipment therefor, and these are devised so as to elevate the crystallization ratio. A low crystallization ratio means the return of a large volume of a mother liquor into the equipment for cooling and crystallization, involving the increase of the circulating raffinose in the production system, whereby the processability of a starting solution is reduced, leading to the decrease of the final productivity and additionally to a longer retention time of the solution, with the resultant deterioration of the product quality. Therefore, a process of dissolution and are crystallization is sometimes necessary so as to retain given quality. A low crystallization ratio is disadvantageous from the standpoint of production cost, which is overcome by the method for producing raffinose crystal according to the present patent.

What is claimed is:

1. A method for producing raffinose crystal, which comprises
   (1) feeding a solution containing raffinose into a container equipped with a cooling part;
   (2) cooling the solution;
   (3) adding raffinose crystal growing seed thereto; and
   (4) circulating the seed-added solution continuously or intermittently by drawing from the container, passing through a pipe and returning into the container, while cooling the seed-added solution.

2. The method according to claim 1, which is carried out with running an agitator arranged in the container.

3. The method according to claim 2, wherein in step (3) the raffinose crystal growing seed is added when the temperature of the solution is in the range of 35 to 50° C.

4. The method according to claim 3 wherein the solution containing raffinose in step (1) is a solution containing raffinose at a concentration of which the supersaturation degree, at 50–70° C., is 0.5 to 1.0, of which the raffinose purity is 60–99 SD %, and of which the rBx, at 20° C., is 60 or less.

5. The method according to claim 3, wherein wherein the seed-added solution is further cooled from 35 to 50° C. to 18 to 22° C. in approximately inverse proportion to the time over 10 to 50 hours.

6. The method according to claim 2 wherein the solution containing raffinose in step (1) is a solution containing raffinose at a concentration of which the supersaturation degree, at 50–70° C., is 0.5 to 1.0, of which the raffinose purity is 60–99 SD %, and of which the rBx, at 20° C., is 60 or less.

7. The method according to claim 6, wherein wherein the seed-added solution is further cooled from 35 to 50° C. to 18 to 22° C. in approximately inverse proportion to the time over 10 to 50 hours.

8. The method according to claim 2, wherein another solution containing raffinose to which raffinose crystal growing seed has been added, is further added into the container, after the seed addition in step (3), apart from or after mixing with the solution drawn from the container for the circulation, and the resulting solution in the container is circulated similarly.

9. The method according to claim 8, wherein the another solution containing raffinose is a solution containing raffinose at a high concentration.

10. The method according to claim 1, wherein in step (3) the raffinose crystal growing seed is added when the temperature of the solution is in the range of 35 to 50° C.

11. The method according to claim 10, wherein the seed-added solution is further cooled from 35 to 50° C. to 18 to 22° C. in approximately inverse proportion to the time over 10 to 50 hours.

12. The method according to claim 10 wherein the solution containing raffinose in step (1) is a solution containing raffinose at a concentration of which the supersaturation degree, at 50–70° C. is 0.5 to 1.0, of which the raffinose purity is 60–99 SD %, and of which the rBx, at 20° C., is 60 or less.

13. The method according to claim 12, wherein wherein the seed-added solution is further cooled from 35 to 50° C. to 18 to 22° C. in approximately inverse proportion to the time over 10 to 50 hours.

14. The method according to claim 1 wherein the solution containing raffinose in step (1) is a solution containing raffinose at a concentration of which the supersaturation degree, at 50–70° C., is 0.5 to 1.0, of which the raffinose purity is 60–99 SD %, and of which the rBx, at 20° C., is 60 or less.

15. The method according to claim 1, wherein another solution containing raffinose to which raffinose crystal growing seed has been added, is further added into the container, after the seed addition in step (3), apart from or after mixing with the solution drawn from the container for the circulation, and the resulting solution in the container is circulated similarly.

16. The method according to claim 15, wherein the another solution containing raffinose is a solution containing raffinose at a high concentration.

* * * * *